United States Patent [19]

Manolagas

[11] 4,375,459

[45] Mar. 1, 1983

[54] CYTORECEPTOR ASSAY

[75] Inventor: Stavros C. Manolagas, Del Mar, Calif.

[73] Assignee: The Regents of the University of California, Berkeley, Calif.

[21] Appl. No.: 161,462

[22] Filed: Jun. 20, 1980

[51] Int. Cl.$^3$ ...................... G01N 33/56; G01N 33/58
[52] U.S. Cl. .......................................... 435/2; 435/7; 436/504
[58] Field of Search ...................... 424/1, 12; 435/2, 7; 23/230 B

[56] References Cited

U.S. PATENT DOCUMENTS

| | | | |
|---|---|---|---|
| 4,092,116 | 5/1978 | Giaever | 23/230 B |
| 4,247,536 | | Fruitstong et al. | 424/12 |
| 4,282,315 | 8/1981 | Luderer et al. | 23/230 B |

OTHER PUBLICATIONS

Parker, *Radio Immunoassay of Biologically Active Compounds*, Prentice-Hall, Inc., N.J., 1976, pp. 180–189.
Cullen et al., The Journal of Immunology, vol. 117, No. 1, Jul. 1976, pp. 136–142.
Bizollon ed., *Radioimmunology 1979*, Elsevier/North Holland Biomedical Press, Amsterdam, 1979, pp. 161–170.

*Primary Examiner*—Christine M. Nucker
*Attorney, Agent, or Firm*—Bertram I. Rowland

[57] ABSTRACT

Novel assays are provided employing specific ells having cytoreceptors for an analyte. The assay combines the specific cells, the sample, and a tagged analyte, normally radioactively tagged. After a sufficient time, the cells are separated, conveniently by centrifugation, and either the supernatant or the cells assayed for the signal resulting from the tag.

14 Claims, No Drawings

CYTORECEPTOR ASSAY

BACKGROUND OF THE INVENTION

1. Field of the Invention

During the last decade, research on vitamin D has lead to the recognition that vitamin D is the precursor of a new steroid hormone, namely 1,25-dihydroxyvitamin D. This is the substance which controls the translocation of calcium through the cells of instestine, bone and kidney. Efforts to measure this hormone have encountered difficulties, because of its instability, low concentration (normal levels 0–40 pg/ml) and, more significantly, because of the necessity for its separation from other metabolites of vitamin D of similar structure which circulate at much higher levels (25(OH)D$_3$-normal levels of 20–40 ng/ml; 24,25(OH)$_2$D$_3$-normal levels 2–5ng/ml).

While assays have been developed, they have proven laborious, expensive and time consuming, requiring expensive equipment and highly skilled personnel. Therefore, these assays have not found acceptance except in few research centers.

2. Description of the Prior Art

Methods for measuring 1,25-dihydroxyvitamin D$_3$ are described in Brumbaugh et al., Biochem. 1974; 13:4091–4097; Clemens et al., Clin. Sci. Mol. Med. 1978; 54:329–332; Schaefer and Goldsmith, in Normann, et al., Eds. Vitamin D Basic Research and Its Clinical Application, New York, Walter de Gruyter, 1979, pages 205–212.

SUMMARY OF THE INVENTION

Cells having cytoreceptors for a specific analyte are used in assays for the analyte. The assay is performed by combining the cells, the sample, and tagged analyte, conventionally radioactively tagged, in an appropriate assay medium and incubating for a sufficient time, for a portion of the analyte to bind to the cells. The cells are then separated and the amount of label in the supernatant or in the precipitate determined and compared to a standard, where the assay has been carried out with a known amount of analyte.

DESCRIPTION OF THE SPECIFIC EMBODIMENTS

Assays are provided employing cells which have a cytoreceptor protein which allows for distinguishing between an analyte of interest and other compounds which may be present in the assay medium. The two prime assay components are the cells and the tagged analyte.

The cells which are employed are specific for a compound in the sense that other compounds which are present will not affect the amount of analyte which enters the cells. The cytoreceptor can distinguish the analyte of interest from closely analogous compounds. The cytoreceptor may be on the surface of the cell, as part of the membrane or in the cytosol. Where the cytoreceptor is in the cytosol, the membrane may cooperate with the cytoreceptor in allowing for preferred transport through the membrane of the analyte of interest as compared to transport of close analogs.

Conveniently, mammalian tumor cells may be employed which can readily be grown in vitro. By obtaining an appropriate cell line which is capable of in vitro culturation, the desired cells can be continuously grown. Depending on the nature of the cell, malanomas, sarcomas, carcinomas, and the like may be employed.

The analyte may be any hapten or protein for which a cytoreceptor is available. Compounds of particular interest include hormones, steroids, both hormonal and non-hormonal, peptides, or any other drug for which a specific cytoreceptor can be found or developed.

Since many compounds of physiological interest act as effectors by binding to a site at the cell surface, any compound which can be bound to a cytoreceptor may be assayed. Therefore, naturally occurring compounds can be assayed, such as a wide variety of peptides and proteins, as well as modified analogs of naturally occurring compounds, such as derivatized or chemically modified steroids, antibiotics, and physiologically mimetic analogs, such as opiates, meperidine, catecholamine, benzdiazepines, dibenzazepines, and barbitals.

In particlar, the hormones 1,25-dihydroxyvitamin D$_2$ and D$_3$ are of interest. For these hormones, bone cells can be employed as the cytoreceptors, particularly osteogenic sarcoma cells.

So far as the tagged analyte, any tag may be employed which will not interfere with the binding of the tag to the cytoreceptor. Where the cytoreceptor is on the surface or in the membrane, the tag must not interfere with the binding of the analyte to the binding site. Where the receptor is in the cytosol, the tag must not interfere with the passage of the tagged analyte through the membrane for entry into the cell.

Tags of particular interest are radioactive tags, such as $^3$H, $^{125}$I, $^{32}$P, and the like. The particular radioactive tag will vary in accordance with the nature of the analyte and synthetic convenience in tagging the analyte. The manner in which radioactive tags are bound to various analytes is amply described in the literature, conventional and need not be described here.

In carrying out the assay, for example, the cells and the tagged analyte are combined in the appropriate assay medium. The medium will normally be buffered at a pH in the range of about 5 to 10, more usually about 6 to 9, and a wide variety of buffers may be employed. Illustrative buffers include carbonates, phosphate, tris, piperazine salts, etc. The concentration of buffer will generally range from about 0.05 M to 0.5 M, depending upon the desired ionic strength, the nature of the sample, the degree of buffering required, and the like. Other additives which may be included are cell growth inhibitors, stabilizers, neutral salts, nutrients and the like.

The assay medium will be a proteinaceous medium to support cell viability. Conveniently, minimum essential medium will be employed, or other common supportive medium. Other additives may also be included, such as fetal calf serum, human alpha-globulin Fraction IV (which is rich in vitamin D binding protein), or the like. The particular medium is not critical and may be varied in conjunction with the nature of the cells.

The particular order of combination of components is not significant, except that the tagged analyte may not be combined with the cells, prior to contacting the cells with the sample. Therefore, the cells and sample may be contacted first, followed by the addition of the tagged analyte or alternatively, the sample and tagged analyte combined either concomitantly with or prior to the addition of the cells.

The temperature of incubation will generally be from about 20° to 50°, more usually from about 25° to 40° C., preferably from about 30° to 45° C. The time of incubation with the cells will generally vary from about 5 min to 24 hrs, more usually from 0.5 hr to 6 hrs. The time will be dependent upon the sensitivity of the assay, the concentration and nature of the analyte, the rate at which the analyte binds to and/or enters the cells, and the like. For the most part, the time will be chosen empirically to provide for a sufficient differentiation in signal over the range of interest of the analyte. During incubation, the medium will be mildly agitated to prevent cell sedimentation.

The radioactively tagged analyte will generally be not more than about five times, more usually not more than about equal, to the minimum concentration of analyte of interest in the assay medium and may be $10^{-3}$ or less than that concentration. The choice will depend upon the label employed, the ability to measure differences in the amount of label, the concentration of analyte in the range of interest, and the like.

The number of cells employed will usually be determined empirically based on the particular analyte, the time period for the assay, the rate of transmission of the analyte through the membrane into the cell, as well as other factors which affect the sensitivity of the assay.

With 1,25(OH)$_2$D$_3$, the number of cells will be not less than about $10^3$, usually $10^4$, times the number of picograms of 1,25(OH)$_2$D$_3$ at the upper end of the concentration range of interest and not more than about $10^8$, usually not more than about $10^7$ times, the number of picograms at the lower range of interest. The particular amount chosen will vary between the extremes.

The assay volume should be as small as convenient for manipulation without contributing significant mechanical errors. Usually the assay volume will be at least about 0.1 ml, more usually at least about 0.2 ml and not exceed about 1 ml. The amount of physiological fluid will be under 1 ml, generally ranging from about 0.05 ml to about 0.6 ml, depending on the analyte. The physiological fluid can be plasma, serum, urine, spinal fluid, saliva or the like.

After incubation, separation of the cells may be achieved by mechanical means, mild centrifugation, or other means, such as immunological binding to a surface, or use of a marker which permits separation e.g. a cell sorter.

After the cells are separated from the liquid medium, the cells will normally be washed to remove any non-specific binding. Conveniently an isotonic solution is employed containing a small amount of an inert protein e.g. albumin, generally about 0.1 to 5 mg/ml, more usually 0.5 to 2 mg/ml. The cells are then sonicated in an appropriate mildly reducing hypertonic buffer, centrifuged and the supernatant assayed for the signal label.

The following examples are offered by way of illustration and not by way of limitation.

Osteogenic sarcoma cells (Martin et al. Clin. Orthop. Rel. Res. 1979; 140:247-254) were subcultured (Manolagas, et al., J. Biol. Chem. 1980; 255:4414-4417). (Freshly thawed DMSO frozen cells acted identically to fresh cells.) Confluent cells freed by trypsinization are suspended in minimum essential medium with Hanks salts, 25 mM Hepes and 2% fetal calf serum at a concentration of $3.3 \times 10^6$ cells/ml. (Human alpha-globulin Fraction IV, 4 mg/ml may be substituted for fetal calf serum.)

Approximately 5,000 cpm (20 pg) of [$^3$H]1,25-(OH)$_2$D$_3$ (NEN, 160 Ci/mmol) in ethanol are pipetted into polycarbonate tubes, by itself and with varying amounts of unlabeled 1,25(OH)$_2$D$_3$ (4-128 pg) and the ethanol removed with a gentle stream of dry N$_2$. To each tube is then added 0.3 ml (0.15 ml can also be used and the counts doubled) of cell suspension ($1 \times 10^6$ cells) and the medium incubated for 1 hr at 37° C., while agitating the tubes with a vortexing platform to prevent sedimentation.

At completion of the incubation, the tubes are cooled on ice and the cells pelleted by centrifugation (RC3 Sorvall centrifuge 5 min, 2,000 rpm). The medium is then aspirated and the cells washed once with 3.5 ml isotonic buffer (0.25 M surcrose, 0.025 M KCl, 0.005 M MgCl$_2$, 0.001 M EDTA, 0.012 M thioglycerol and 0.05 M Tris-HCl, pH 7.4; desirably 1 ml/ml bovine serum albumin is included). After the addition of 1 ml hypertonic buffer (0.3 MKCl, 0.005 M dithiothreitol, 0.0015 M EDTA, and 0.01 M Tris-HCl, pH 7.4) to each tube, the cells are sonicated with $1 \times 5$ second bursts of a sonifier cell disruptor (Heat Systems-Ultrasonics Inc.). After centrifuging for 0.5 hr at 40,000 RCF in a RC-2B Sorvall centrifuge (SM-24 rotor) An RC-3 Sorvall centrifuge at 3,500 rpm for 1 hr was found satisfactory), the supernatant is then transferred to counting vials and counted with 10 ml of scintillation liquid.

A satisfactory standard curve was obtained over the concentration range indicated above, with the number of cpm being about 1290 at 0pg unlabelled 1.25(OH)$_2$D$_3$ and about 690 at 128 pg unlabelled 1,25(OH)$_2$D$_3$.

In accordance with the subject invention an extremely sensitive assay is provided for determining physiological compounds in the presence of related compounds. By employing tumor cells which can be cultured in vitro and are specific for a wide variety of physiologically active compounds, the natural binding affinity of cells may be used for assaying for very low concentrations of substances of interest.

Although the foregoing invention has been described in some detail by way of illustration and example for purposes of clarity of understanding, it will be obvious that certain changes and modifications may be practiced within the scope of the appended claims.

I claim:

1. A method for determining an analyte capable of specifically binding to a cytosol cell receptor, said method comprising:

combining in a liquid assay medium supportive of cell viability, a sample suspected of containing said analyte, cells having a specific extracellular receptor for said analyte, and tagged analyte, wherein the tag provides a detectable signal;

after a sufficient time for said analyte and tagged analyte to bind to said cells, separating said cells from said liquid assay medium, substantially free of non-specifically bound tagged an analyte; and determining the amount of tagged analyte bound to said cells by means of said detectable signal, as compared to the amount of tagged analyte determined in an assay with a known amount of analyte.

2. A method according to claim 1, wherein said tag is a radioactive isotope.

3. A method according to claim 1, wherein said binding of said analyte and tagged analyte to said cells is at a temperature in the range of about 20° to 50° C.

4. A method for determining an analyte capable of specifically binding to a cytosol receptor, said method comprising:

combining in a buffered liquid nutrient assay medium supportive of cell viability a sample suspected of containing said analyte, cells having a specific intracellular receptor for said analyte and analyte tagged with a radioactive isotope;

incubating said mixture at a temperature in the range of about 30° to 45° for a time sufficient for analyte and tagged analyte to bind to said cells;

separating said cells substantially free of non-specifically bound tagged analyte from said liquid medium;

disrupting said cells in liquid medium and separating the resulting cell debris from said liquid medium to provide a supernatant liquid; and determining the amount of radioisotope in the supernatant as compared to a supernatant obtained with a known amount of analyte.

5. A method according to claim 4, wherein said cells are tumor cells.

6. A method according to claim 5, wherein said cells are osteogenic sarcoma cells.

7. A method according to claims 4 or 6, wherein said analyte is 1,25-dihydroxyvitamin $D_3$ and 1,25-dihydroxyvitamin $D_2$.

8. A method according to claim 7, wherein said liquid assay medium includes alpha-globulin Fraction IV.

9. An assay composition for use in a method according to claim 1, comprising: (a) mammalian tumor cells having a specific intracellular receptor for an analyte; and (b) tagged analyte.

10. An assay composition according to claim 9, wherein said analyte is 1,25-dihydroxy-vitamin $D_3$.

11. An assay composition according to claim 9, wherein said analyte is 1,25-dihydroxy-vitamin $D_2$.

12. An assay composition according to any of claims 9, 10 or 11, wherein said tag is a radionuclide.

13. An assay composition according to claim 9, wherein said analyte is a hormone.

14. An assay composition according to claim 13, wherein said hormone is a steroid.

* * * * *

UNITED STATES PATENT AND TRADEMARK OFFICE
CERTIFICATE OF CORRECTION

PATENT NO. : 4,375,459
DATED : March 1, 1983
INVENTOR(S) : Stavros C. Manolagas

It is certified that error appears in the above—identified patent and that said Letters Patent is hereby corrected as shown below:

Col. 4, line 48, change "extracellular" to --intracellular--.

Signed and Sealed this

Thirteenth Day of December 1983

[SEAL]

Attest:

GERALD J. MOSSINGHOFF

Attesting Officer     Commissioner of Patents and Trademarks